(12) United States Patent
Murry et al.

(10) Patent No.: US 7,875,451 B2
(45) Date of Patent: Jan. 25, 2011

(54) FORMULATION TO IMPROVE SURVIVAL OF TRANSPLANTED CELLS

(75) Inventors: Charles E. Murry, Seattle, WA (US); Michael Alan Laflamme, Seattle, WA (US)

(73) Assignee: The University of Washington, Seattle, WA (US)

( * ) Notice: Subject to any disclaimer, the term of this patent is extended or adjusted under 35 U.S.C. 154(b) by 782 days.

(21) Appl. No.: 11/336,502

(22) Filed: Jan. 19, 2006

(65) Prior Publication Data

US 2007/0166288 A1    Jul. 19, 2007

(51) Int. Cl.
C12N 5/00    (2006.01)
C12N 5/02    (2006.01)

(52) U.S. Cl. ................................................. 435/325

(58) Field of Classification Search .................. 435/325
See application file for complete search history.

(56) References Cited

U.S. PATENT DOCUMENTS

| | | | | |
|---|---|---|---|---|
| 5,354,764 | A * | 10/1994 | Grover et al. | 514/353 |
| 6,437,097 | B1 * | 8/2002 | Hsueh et al. | 530/388.1 |
| 2001/0053354 | A1 * | 12/2001 | Dinsmore | 424/93.7 |
| 2005/0054092 | A1 * | 3/2005 | Xu et al. | 435/366 |
| 2005/0058630 | A1 * | 3/2005 | Harris et al. | 424/93.7 |

OTHER PUBLICATIONS

Suzuki et al., Circulation, 2000, 102, suppl III:III-216-221.*

Contreras, J., et al, "Cytoprotection of pancreatic islets before and early after transplantation using gene therapy," (2002) *Kidney International*, 61(Symposium 1):S-79—S-84.

Fearnhead, H,, et al., "A pre-existing protease is a common effector of thymocyte apoptosis mediated by diverse stimuli," (1995) *FEBS Letters*, 357:242-246.

He, J., et al., "Human embryonic stem cells develop into multiple types of cardiac myocytes: action potential characterization," (2003) *Circulation Research*, 93:32-39.

Jackson, K., et al., "Regeneration of ischemic cardiac muscle and vascular endothelium by adult stem cells," (2001) *The Journal of Clinical Investigation*, 107(11):1395-1402.

Kehat, I., et al., "Human embryonic stem cells can differentiate into myocytes with structural and functional properties of cardiomyocytes," (2001) 108(3):407-414.

Kleinman, H., et al., "Matrigel: Basement membrane matrix with biological activity," (2005) *Elsevier Seminars in Cancer Biology*, 15:378-386.

Laflamme, M., et al., "Formation of human myocardium in the rat heart from human embryonic stem cells," (2005) *American Journal of Pathology*, 167(3):663-671.

Malhotra, R., et al., "Glucose uptake and glycolysis reduce hypoxia-induced apoptosis in cultured neonatal rat cardiac myocytes," (1999) *The Journal of Biological Chemistry*, 274(18)12567-12575.

Mehrhof, F., et al., "In cardiomyocyte hypoxia, insulin-like growth factor-l-induced antiapoptotic signaling requires phosphatidylinositol-3-OH-kinase-dependent and mitogen-activated protein kinase-dependent activation of the transcription factor cAMP response element-binding protein," (2001) *Circulation* 104:2088-2094.

Mummery, C., et al., "Cardiomyocyte differentiation of mouse and human embryonic stem cells," (2002) *Journal of Anatomy* 200:233-242.

Mummery, C., et al., "Differentiation of human embryonic stem cells to cardiomyocytes: role of coculture with visceral endoderm-like cells," (2003) *Circulation* 107:2733-2740.

Oh, H., et al., "Cardiac progenitor cells from adult myocardium: homing, differentiation, and fusion after infarction," (2003) *PNAS*, 100(21)12313-12318.

Reinecke, H., et al., "Electromechanical coupling between skeletal and cardiac muscle: implications for infarct repair," 149(3):731-740.

Reinecke, H., et al., "Skeletal muscle stem cells do not transdifferentiate into cardiomyocytes after cardiac grafting," (2002) *Journal of Molecular Cell Cardiology* 34:241-249.

Reiss, K., et al., "Insulin-like growth factor-1 receptor and its ligand regulate the reentry of adult ventricular myocytes into the cell cycle," (1997) *Experimental Cell Research*, 235:198-209.

Schierle, G., et al., "Caspase inhibition reduces apoptosis and increases survival of nigral transplants," (1999) *Nature Medicine* 5(1):97-100.

Shim, et al., "Stem cell cardiomyoplasty: state-of-the-art," (2004) *Annals Academy of Medicine Singapore*, 33(4):451-460.

Shimizu, S., et al., "BH4 domain of antiapoptotic Bcl-2 family members closes voltage-dependent anion channel and inhibits apoptotic mitochondrial changes and cell death," (2000) *PNAS*, 97(7):3100-3105.

(Continued)

*Primary Examiner*—Ruth A Davis
(74) *Attorney, Agent, or Firm*—Bozicevic, Field & Francis LLP; Pamela J. Sherwood

(57) ABSTRACT

The survival of cells during transplantation is enhanced. Cells to be transplanted are administered in a formulation that provides two ore more survival enhancing factors. Optionally, prior to administration, the cells are cultured in the presence of factors that enhance survival, and may be heat shocked prior to transplantation.

18 Claims, 1 Drawing Sheet
(1 of 1 Drawing Sheet(s) Filed in Color)

OTHER PUBLICATIONS

Skuk, D., et al., "Resetting the problem of cell death following muscle-derived cell transplantation: detection, dynamics and mechanisms," (2003) *Journal of Neuropathology and Experimental Neurology*, 62(9):951-967.

Szmitko, P., et al., "Endothelial Progenitor Cells," (2003) *Circulation*, 107:3093-3100.

Tomita, S., et al., "Autologous transplantation of bone marrow cells improves damaged heart function," (1999) *Circulation*, 100:II-247—II-256.

Vanden Hoek, T., et al., "Preconditioning in cardiomyocytes protects by attenuating oxidant stress at reperfusion," (2000) *Circulation Research*, 2000(86):541-548.

Zandstra, P.W., et al., "Scalable production of embryonic stem cell-derived cardiomyocytes," (2003) *Tissue Engineering*, 9(4):767-778.

Zhang, M., et al., "Cardiomyocyte grafting for cardiac repair: graft cell death and anti-death strategies," (2001) *Journal of Molecular Cell Cardiology*, 33:907-921.

Zimmerman, W., et al., "Cardiac grafting of engineered heart tissue in syngenic rats," (2002) *Circulation*, 106(Suppl I):I-151—I-157.

* cited by examiner

FORMULATION TO IMPROVE SURVIVAL OF TRANSPLANTED CELLS

This invention was made with Government support under contracts K08 HL080431-01; P01 HL03174; R01 HL61553; R24 HL64387; P20 GM69983 awarded by the National Institutes of Health. The Government has certain rights in this invention.

This invention relates generally to the field of cell biology of engraftment. More specifically, this invention provides methods for the improving the survival of cells during the engraftment process.

BACKGROUND OF THE INVENTION

Muscle is one of the largest tissues in the body, and one that can be subjected to severe mechanical and biological stresses. A number of widespread and serious conditions cause necrosis of heart tissue, leading to unrepaired or poorly repaired damage. For example, coronary artery disease, in which the arteries feeding the heart narrow over time, can cause myocardial ischemia, which if allowed to persist, leads to heart muscle death. Another cause of ischemia is myocardial infarction (MI), which occurs when an artery feeding the heart suddenly becomes blocked. This leads to acute ischemia, which again leads to myocardial cell death, or necrosis.

Cardiac tissue death can lead to other heart dysfunctions. If the pumping ability of the heart is reduced, then the heart may remodel to compensate; this remodeling can lead to a degenerative state known as heart failure. Heart failure can also be precipitated by other factors, including valvular heart disease and cardiomyopathy. In certain cases, heart transplantation must be used to replace an ailing heart.

Unlike skeletal muscle, which regenerates from reserve myoblasts called satellite cells, the mammalian heart has a very limited regenerative capacity and, hence, heals by scar formation. The severity and prevalence of these heart diseases has led to great interest in the development of progenitor and stem cell therapy, which could allow the heart to regenerate damaged tissue and ameliorate cardiac injury. For human therapeutic application, a suitable myogenic cell type from either an autologous or appropriately matched allogeneic source may be delivered to the infarcted zone to repopulate the lost myocardium.

A number of different cell types have been considered for such therapies, including somatic cells as diverse as hematopoietic stem cells; mesenchymal stem cells; and even peripheral blood cells. Included in cells for therapy are cells derived from embryonic stem cells (ES cells). ES cells have the capacity to give rise to all tissues, including those for which no somatic stem cells are known, such as cardiac muscle (see Kehat et al. (2001) J. Clin. Invest. 108:407-414; Mummery et al. (2002) J. Anat. 200:233-242; he et al. (2003) Circ. Res. 93:32-39). ES cells have certain advantages for cardiac repair applications. There are well-defined protocols for the isolation and maintenance of ESCs, and they have a tremendous capacity for in vitro expansion, making them scalable for human applications (Zandstra et al. (2003) Tissue Eng. 9:767-778). Human ESC-derived cardiomyocytes possess the cellular elements required for electromechanical coupling with the host myocardium, such as gap and adherens junctions, and it is therefore expected that, when transplanted, these cells could electrically integrate and contribute to systolic function (see Mummery et al. (2003) Circulation 107:2733-2740). This property represents a significant advantage over other cell types, such as skeletal muscle, which act through modulation of diastolic function (see Reinecke et al. (2000) J. Cell. Biol. 149:731-740; and Reinecke et al. (2002) J. Mol. Cell. Cardiol. 34:241-249).

In brief, for human therapeutic application, a suitable myogenic cell type from either an autologous or appropriately matched allogeneic source may be delivered to the infarcted zone to replace the lost myocardium. Unfortunately, the efficacy of all potential cardiac cell therapies at present is that they are greatly limited by the subsequent death of the implanted cells.

Cell death after cardiac grafting is described by Zhang et al. (2001) J Mol Cell Cardiol 2001, 33:907-921, and similar phenomena are known to occur upon cell grafting in other tissues, for example, islet cells for diabetes (Contreras et al. (2002) Kidney Int, 61:79-84), dopaminergic neurons for Parkinson's disease (Schierle et al. (1999) Nat Med, 5:97-100), and skeletal myoblasts for muscular dystrophy (Skuk et al. (2003) J Neuropathol Exp Neurol, 62:951-967).

In cardiac engraftment, the magnitude and time course of cell death of rat neonatal cardiomyocytes implanted into the hearts of syngeneic hosts was examined by Zhang et al. Cell death was found to peak at 1 day, remain elevated at 4 days, and had largely subsided by 7 days. An estimated 90-99% of the graft myocytes had died within this first week. Importantly, increasing the number of implanted cells did not improve the outcome but instead simply increased the death rate. The underlying causes of cell death after cardiac delivery are not completely elucidated.

Methods of improving graft survival, particularly survival of progenitor cell grafts, is of great clinical interest. The present invention addresses this issue.

SUMMARY OF THE INVENTION

Composition and methods are provided for increasing the survival of cells during the process of transplantation. Cells are transferred into a recipient host in a formulation that provides two or more survival enhancing factors. Optionally, prior to transfer into the recipient, the cells are cultured in the presence of factors that enhance survival, and may be heat shocked prior to transfer. Cells of interest include progenitor cells, which may be derived from tissue sources of progenitor cells or may be derived from the differentiation of suitable stem cells, including embryonic stem cells. In one embodiment of the invention, the cells are cardiomyocytes, or progenitors thereof. Such cardiomyocytes may be derived from an in vitro culture of embryonic stem cells.

The formulation of cells for injection is a fluid suspension that comprises at least two survival enhancing factors chosen from: solubilized extracellular matrix; an immunosuppressive agent; a caspase inhibitor; an anti-apoptotic agent; an IGF1R ligand; and a $K_{ATP}$ channel opening agent. In one embodiment of the invention the formulation comprises three or more of such agents; four or more, five; or six such agents. The formulation may further comprise such buffers and additives as required for maintenance of cell viability.

In one embodiment, methods are provided for transplantation, the method comprising injecting into a recipient a formulation of cells comprising at least two survival enhancing factors. The method may further comprise the step of heat shocking said cells prior to transfer into the recipient. Optionally, prior to transfer into the recipient, the cells are cultured for a period of time in medium comprising at least one survival factor. Optionally, the method further comprises detection of viable cells following said transfer. Optionally, the method further comprises administering an anti-inflammatory agent for a period of time following said transfer.

In another embodiment, compositions are provided for use in transplantation. Such compositions may comprise a cocktail of two or more survival enhancing factors, in a form suitable for combining with cells prior to transfer into a recipient. Such a composition may further comprise suitable buffers and/or excipients appropriate for transfer into an animal. Such compositions may further comprise cells to be engrafted. Such cells are optionally heat shocked prior to combining with said survival factors. Such cells are optionally cultured for a period of time in medium comprising at least one survival factor.

These and other embodiments of the invention will be apparent from the description that follows. The compositions, methods, and techniques described in this disclosure hold considerable promise for use in diagnostic, drug screening, and therapeutic applications.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
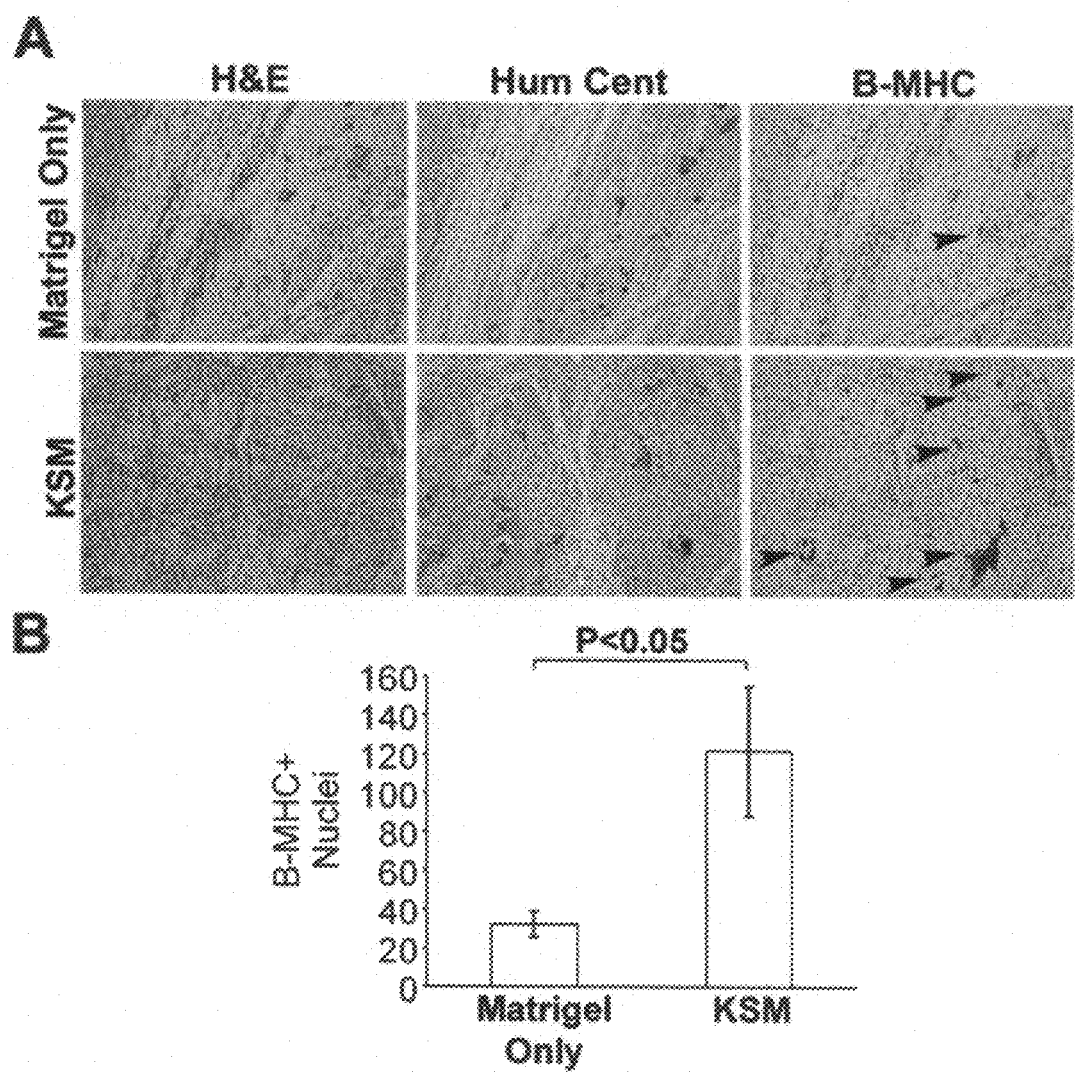
FIGS. 1A-1B. KSM results in larger human myocardial implant. Previously infarcted athymic rats received control hESC-derived cardiomyocytes or identical cells, either in Matrigel only (n=6) or "KSM" cocktail. Hearts were harvested after 1 week and evaluated histologically using routine H&E, in situ hybridization with a human-specific pan-centromeric probe (Hum Cent), or immunohistochemistry with the human-specific cardiac marker β-myosin heavy chain (B-MHC). No human cells were detected in the recipients of untreated control cells (n=4 recipients). 5 of 5 recipients of cells in Matrigel showed human graft cells, although relatively few human cardiac cells were identified. 6 of 6 recipients of cells in KSM showed human graft cells, and a substantial cardiac component was present in each. A: Adjacent sections stained with the aforementioned markers, taken from representative hearts receiving Matrigel only or KSM-treated cells. 200× objective. B: Recipients of KSM-treated cells showed a mean four-fold larger graft (quantified as total B-MHC+ nuclei) than with Matrigel alone.

Composition and methods are provided for increasing the survival of cells during the process of transplantation. Cells to be transplanted are administered in a formulation that provides two or more survival enhancing factors. Optionally, prior to administration, the cells are cultured in the presence of one or a plurality of survival enhancing factors, and may be heat shocked prior to injection. Cells of interest for transplantation include progenitor cells, which may be derived from tissue sources of progenitor cells or may be derived from the differentiation of suitable stem cells, including embryonic stem cells. In one embodiment of the invention, the cells are cardiomyocytes, or progenitors thereof. Throughout this disclosure, techniques and compositions that refer to "cardiomyocytes" or "cardiomyocyte precursors" can be taken to apply equally to cells at any stage of cardiomyocyte ontogeny without restriction, as defined above, unless otherwise specified. The cells may or may not have the ability to proliferate or exhibit contractile activity.

The formulation of cells for injection is a fluid suspension that comprises at least two survival enhancing factors chosen from: solubilized extracellular matrix; an immunosuppressive agent; a caspase inhibitor; an anti-apoptotic agent; an IGF1R ligand; and a $K_{ATP}$ channel opening agent. Where two survival factors are present, such factors may comprise solubilized extracellular matrix and an immunosuppressive agent; solubilized extracellular matrix and a caspase inhibitor; solubilized extracellular matrix and an anti-apoptotic agent; solubilized extracellular matrix and an IFG1R ligand; solubilized extracellular matrix and a $K_{ATP}$ channel opening agent. Where three survival factors are present, such factors may comprise solubilized extracellular matrix in combination with two agents chosen from an immunosuppressive agent; a caspase inhibitor; an anti-apoptotic agent; an IGF1R ligand; and a $K_{ATP}$ channel opening agent. Specific examples and guidelines for selection of an agent within each class of survival factor is disclosed herein.

In one embodiment, the cells to be transplanted are provided as a suspension, which may be a single cell suspension, or a suspension of small clumps of cells, e.g. of about 2, 5, 10, 20 or fewer cells, usually not more than about 100 cells, and which are distinguished from solid tissue grafts, which are implanted and are not injected or infused. The cell suspension is a form that can be injected or infused into a recipient. In another embodiment, the cells are provided as an ex vivo engineered tissue construct.

The methods and compositions of the invention provide for increased survival of cells after they are administered to a recipient animal. In experimental systems, survival of cells may be measured after short periods of time, e.g. after at least about three to about seven days. When measured over such a time period, the methods of the invention provide for an increase in cell survival of at least about 5-fold, at least about 10-fold, at least about 20-fold, at least about 50-fold, at least about 100-fold, or more, relative to transplantation in the absence of the factor(s).

A cell transplant, as used herein, is the transplantation of one or more cells into a recipient body, usually for the purpose of augmenting function of an organ or tissue in the recipient. As used herein, a recipient is an individual to whom tissue or cells from another individual (donor), commonly of the same species, has been transferred. Generally the MHC antigens, which may be Class I or Class II, will be matched, although one or more of the MHC antigens may be different in the donor as compared to the recipient. The graft recipient and donor are generally mammals, preferably human. Laboratory animals, such as rodents, e.g. mice, rats, etc. are of interest for drug screening, elucidation of developmental pathways, etc. For the purposes of the invention, the cells may be allogeneic, autologous, or xenogeneic with respect to the recipient.

Cells of interest for transfer include, without limitation, cardiomyocytes and progenitors thereof; neural progenitor cells, e.g. for the regeneration of neurons, or retina, and the like; pancreatic islet cells, particularly pancreatic β-cells; hematopoietic stem and progenitor cells; mesenchymal stem cells; muscle satellite cells; endothelial cells or progenitors thereof; and the like. Tissues of interest include brain tissue; spinal cord tissue; kidney tissue; pancreatic islets; retinal tissue; and the like.

Survival Factors. As used herein, the term survival factors refers to biologically active agents that are provided in a formulation for the suspension of cells prior to transplantation. The presence of survival factor(s) enhances the survival of cells after the cells are transferred into the body of a recipient. Survival factors may be utilized as one or a cocktail of factors. In some embodiments, the survival factors are also utilized as culture additives for a period of time prior to transplantation.

Solubilized extracellular matrix protein comprises structural proteins such as laminin and collagen in a fluid form. The proteins are typically available in a concentrated liquid form, e.g. at about 8 mg/ml to about 15 mg/ml. Such proteins typically comprise laminin, collagen IV and entactin. Commercial preparations of such proteins are available, e.g. as matrigel, hydrogel, etc., or may be produced from basement membrane preparations using methods known in the art, with recombinant protein expression, and the like. The extracellular matrix proteins, when present, are included in the formulation at a final concentration of at least about 2.5 mg/ml, usually at least about 3.5 mg/ml, and may be present at a concentration of at least about 4.5 mg/ml, at least about 5 mg/ml %; and usually not more than about 8 mg/ml %, usually not more than about 6 mg/ml %.

Caspase inhibitor. As used herein, a caspase inhibitor is an agent that inhibits either the upstream initiator caspases (e.g. Caspase-1, -8 or -9), the downstream executioner caspases (Caspase-3, -6 or -7), or preferably both classes (pan-Caspase inhibitor). Caspase-3 has a central role in the execution of apoptosis and may provide a target for regulating cell death. Caspase inhibitors are known and used in the art, including B-D-FMK (pan caspase inhibitor), Z-DEVDFMK (predominantly Caspase-3 inhibitor); Z-VAD-FMK (predominantly Caspase-1 and -3 inhibitor, see Misaghi, S., et al. 2004. *Chem. Biol.* 11, 1677); Ac-VAD-CHO (see Thornberry, N. A., and Lazebnik, Y. 1998. *Science* 281, 1312); IDN-6556. Caspase inhibitors are included at a dose effective to substantially inhibit caspase activity present in the cells to be transplanted. The concentration will vary depending on the specific inhibitor that is used, and may be at least about 1 µM; at least about 5 µM; at least about 25 µM; and not more than about 500 µM, usually not more than about 100 µM; or not more than about 50 µM.

IGF1R ligand. The IGF-1 receptor (IGF1R) is a tyrosine kinase receptor that is functionally and structurally related to the insulin receptor. The IGF1R is activated both by IGF-1 and IGF-2 but not by insulin at physiological concentrations. In some embodiments of the invention, the ligand is IGF-1. Insulin-like growth factor-1 (IGF-1) is a single-chain polypeptide of 70 amino acids. In other embodiments, the ligand is IGF-2. Alternatively, any molecule, e.g. a polypeptide molecule that binds to and activates the IGF1R receptor may be used for the purposes of the invention (see, for example, Vajdos et al. (2001) Biochemistry 40(37):11022-9). Such synthetic ligands may include antibodies and derivatives thereof, e.g. Fc fragments, single chain analogs, etc., and the like. The concentration of the ligand will be dependent on the nature of the ligand. Where the ligand is IGF-1, the concentration will usually be at least about 1 ng/ml, usually at least about 10 ng/ml, at least about 50 ng/ml, at least about 100 ng/ml, and not more than about 1 µg/ml. Where the ligand is other than IGF-1, the concentration will provide equivalent activity to such concentrations of IGF-1.

Anti-apoptotic agent. In addition to the caspase inhibitor, other anti-apoptotic agents may be included in the formulation. In some embodiments of the invention, either a caspase inhibitor or another anti-apoptotic agent is present in the formulation. In another embodiment, both are present. Agents of interest include agents that act in the Bcl pathway of apoptosis. Such agents include the BH4 peptide domain of Bcl-$X_L$ and other BH4 domain polypeptides. Bcl-2 homology domains are found in proteins that inhibit apoptosis such as Bcl-2, Bcl-XL and Bcl-XW. Such BH4 domains and variants thereof are known in the art, e.g. see Huang et al. (1998) The EMBO Journal (1998) 17, 1029-1039, herein incorporated by reference. Soluble forms of BH4 domains are preferred. The agent is provided at a concentration that is effective in inhibiting Bcl pathway mediated apoptosis, and may be measured, for example, by determining the block of the mitochondrial voltage-dependent anion channel (see Shimizu et al. (2000) Proc Natl Acad Sci USA 97:3100-3105). Effective concentrations of Bcl-XL BH4 domain range from at least about 0.1 nM, at least about 1 nM, at least about 10 nM, and not more than about 10 µM, usually not more than about 1 µM or not more than about 100 nM. Where the agent is other than Bcl-XL BH4, the concentration will provide equivalent activity to such concentrations of Bcl-XL BH4.

Anti-inflammatory agent Agents of interest are immunosuppressive agents, and include, without limitation, rapamycin, FK506, cyclosporine A, azathioprine, mycophenolate mofetil; and the like, which agents are widely known and used in the art. In some embodiments of the invention, the agent is a ligand for cyclophilin D, e.g. cyclosporine A, D-43787 (see Pahl et al. (2002) J Pharmacol Exp Ther. 301 (2):738-46); etc. (see Waldmeier et al. (2003) Curr Med Chem. 10(16):1485-506). In one embodiment, the agent is cyclosporine A. Such agents are used at their known effective concentrations. Where the agent is cyclosporine A, the concentration range is at least about 10 nM, usually at least about 50 nM, at least about 100 nM, and not more than about 10 µM, usually not more than about 1 µM. Where the agent is other than cyclosporine A, the concentration will provide equivalent activity to such concentrations of cyclosporine A.

$K_{ATP}$ channel opening agent. Adenosine triphosphate (ATP)-sensitive potassium channels (KATP) exist in cardiac and other tissues and have a potential role in the pathogenesis of myocardial ischemia. KATP channels are composed of a small inwardly rectifying K+ channel subunit, either KIR6.1 or KIR6.2, plus a sulfonylurea receptor, SUR1 or SUR2 (A or B), which belong to the ATP-binding cassette superfamily. Such agents are of particular interest for formulations comprising cardiomyocytes. A number of small molecule KATP openers are known and used in the art. These include, without limitation, cromakalim, pinacidil, diazoxide; A-151892 (in a series of N-[2-(2,2,2-trifluoro-1-hydroxy-1-trifluoromethyl-ethyl)-naphthalen-1-yl]amides); A-312110 ((9R)-9-(4-fluoro-3-iodophenyl)-2,3,5,9-tetrahydro-4H-pyrano[3,4-b]thieno[2,3-e]pyridin-8(7H)-one-1,1-dioxide; and the like. Such agents are used at their known effective concentrations. Where the agent is pinacidil, the concentration range is at least about 1 µM, usually at least about 10 µM, at least about 50 µM, and not more than about 1 mM, usually not more than about 500 µM. Where the agent is other than pinacidil, the concentration will provide equivalent activity to such concentrations of pinacidil.

Heat Shock. In some embodiments of the invention, the cells are heat shocked prior to transplantation. Such a heat shock is typically performed not more than about 48 hours prior to transplantation, usually not more than about 24 hours, and at least about 6 hours, usually at least about least 12 hours prior to transplantation. During the heat shock, the cultured cells are moved from growing temperature to a temperature of from about 40° C. to about 44° C., usually from about 41° C. to about 43° C. for a short period of time, e.g. for about 10 minutes, for about 15 minutes, for about 30 minutes, and for not more than about 60 minutes. The cells may be maintained in the same culture medium, or moved to pre-warmed culture medium.

Stem cells and cultures thereof. Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)).

Stem cells of interest also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shamblott et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2):205-16; etc.) The stem cells may be obtained from any mammalian species, e.g. human, equine, bovine, porcine, canine, feline, rodent, e.g. mice, rats, hamster, primate, etc.

Embryoid bodies are formed by harvesting ES cells with brief protease digestion, and allowing small clumps of undifferentiated human ESCs to grow in suspension culture. Differentiation is induced by withdrawal of conditioned medium. The resulting embryoid bodies can be plated onto semi-solid substrates. Formation of differentiated cells may be observed after around about 7 days to around about 4 weeks.

Optionally, for the generation of cardiomyocytes, cardiotropic factors are included, as described in U.S. Patent application 20030022367, are added to the culture. Such factors may include nucleotide analogs that affect DNA methylation and alter expression of cardiomyocyte-related genes; TGF-β ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFα, and products of the cripto gene; antibodies and peptidomimetics with agonist activity for the same receptors, cells secreting such factors, and the like.

Progenitor or Differentiated Cells. A "differentiated cell" is a cell that has progressed further down the developmental pathway than the cell it is being compared with. Thus, embryonic stem cells can differentiate to lineage-restricted progenitor cells (such as a mesodermal stem cell), which in turn can differentiate into other types of progenitor cells further down the pathway (such as an cardiomyocyte progenitor), and then to an end-stage differentiated cell, which plays a characteristic role in a certain tissue type, and may or may not retain the capacity to proliferate further. For the purposes of the present invention, progenitor cells are those cells that are committed to a lineage of interest, but have not yet differentiated into a mature cell.

Among the differentiated cells of interest are cells not readily grown from somatic stem cells, or cells that may be required in large numbers and hence are not readily produced in useful quantities by somatic stem cells. Such cells may include, without limitation, neural cells, pancreatic islet cells, hematopoietic cells, and cardiac muscle cells. A "cardiomyocyte precursor" is defined as a cell that is capable (without dedifferentiation or reprogramming) of giving rise to progeny that include cardiomyocytes. Such precursors may express markers typical of the lineage, including, without limitation, cardiac troponin I (cTnI), cardiac troponin T (cTnT), sarcomeric myosin heavy chain (MHC), GATA-4, Nkx2.5, N-cadherin, β1-adrenoceptor (β1-AR), ANF, the MEF-2 family of transcription factors, creatine kinase MB (CK-MB), myoglobin, or atrial natriuretic factor (ANF).

Methods of Transplantation

In the methods of the invention, cells to be transplanted are transferred to a recipient in a formulation comprising two or more survival factors as described above. In one embodiment of the invention, the cells are heat shocked prior to transplantation, as described above. Optionally, the cells are cultured in medium comprising an anti-inflammatory agent and IGF1R ligand prior to transplantation, e.g. for at least about 12 hours, at least about 24 hours, at least 48 hours, or more.

In addition to the survival factors described above, the cells are administered in any physiologically acceptable excipient comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium.

Following transplantation, the recipient, including autologous and syngeneic recipients, may be treated with an effective dose of an anti-inflammatory agent for a period of time sufficient for the transplanted cells to survive the initial loss of viability, for example for at least about 3 days, at least about 5 days, at least about 7 days or more.

To determine the suitability of formulations for therapeutic administration, the formulations can first be tested in a suitable animal model. At one level, cells are assessed for their ability to survive and maintain their phenotype in vivo. Cell compositions in formulations of the invention are administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or β-galactosidase); that have been prelabeled (for example, with BrdU or [$^3$H] thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

Where the differentiating cells are cells of the cardiomyocyte lineage, suitability can also be determined in an animal model by assessing the degree of cardiac recuperation that ensues from treatment with the differentiating cells of the invention. A number of animal models are available for such testing. For example, hearts can be cryoinjured by placing a precooled aluminum rod in contact with the surface of the anterior left ventricle wall (Murry et al., J. Clin. Invest. 98:2209, 1996; Reinecke et al., Circulation 100:193, 1999; U.S. Pat. No. 6,099,832). In larger animals, cryoinjury can be inflicted by placing a 30-50 mm copper disk probe cooled in liquid $N_2$ on the anterior wall of the left ventricle for approximately 20 min (Chiu et al., Ann. Thorac. Surg. 60:12, 1995). Infarction can be induced by ligating the left main coronary artery (Li et al., J. Clin. Invest. 100:1991, 1997). Injured sites are treated with cell preparations of this invention, and the heart tissue is examined by histology for the presence of the cells in the damaged area. Cardiac function can be monitored by determining such parameters as left ventricular end-diastolic pressure, developed pressure, rate of pressure rise, rate of pressure decay, and chamber size-based measurements such as end-diastolic dimension, end-systolic dimension, fractional shortening and ejection fraction.

The cell formulations may be used for tissue reconstitution or regeneration in a human patient or other subject in need of such treatment. The cells are administered in a manner that permits them to graft or migrate to the intended tissue site and reconstitute or regenerate the functionally deficient area. Special devices are available that are adapted for administering cells capable of reconstituting cardiac function directly to the chambers of the heart, the pericardium, or the interior of the cardiac muscle at the desired location. The cells may be administered to a recipient heart by intracoronary injection, e.g. into the coronary circulation. The cells may also be administered by intramuscular injection into the wall of the heart.

Medical indications for such treatment include treatment of acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, patient mobility, and quality of life.

Cells may be genetically altered in order to introduce genes useful in the differentiated cell, e.g. repair of a genetic defect in an individual, selectable marker, etc., or genes useful in selection against undifferentiated ES cells. Cells may also be genetically modified to enhance survival, control proliferation, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over a 8-16 h period, and then exchanged into growth medium for 1-2 days. Genetically altered cells are selected using a drug selection agent such as puromycin, G418, or blasticidin, and then recultured.

Kits

The formulations of the invention are optionally packaged in a suitable container with written instructions for a desired purpose. Such formulations may comprise a cocktail of two or more survival enhancing factors, in a form suitable for combining with cells prior to transfer into a recipient. Such a composition may further comprise suitable buffers and/or excipients appropriate for transfer into an animal. Such compositions may further comprise cells to be engrafted. Such cells are optionally heat shocked prior to combining with said survival factors. Such cells are optionally cultured for a period of time in medium comprising at least one survival factor.

For further elaboration of general techniques useful in the practice of this invention, the practitioner can refer to standard textbooks and reviews in cell biology, tissue culture, embryology, and cardiophysiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998). With respect to the culture of heart cells, standard references include The Heart Cell in Culture (A. Pinson ed., CRC Press 1987), Isolated Adult Cardiomyocytes (Vols. I & II, Piper & Isenberg eds, CRC Press 1989), Heart Development (Harvey & Rosenthal, Academic Press 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Example 1

In cardiac engraftment, the magnitude and time course of cell death of rat neonatal cardiomyocytes implanted into the hearts of syngeneic hosts was examined by Zhang et al. Cell death was found to peak at 1 day, remain elevated at 4 days, and had largely subsided by 7 days. An estimated 90-99% of the graft myocytes had died within this first week. Importantly, increasing the number of implanted cells did not improve the outcome but instead simply increased the death rate. The underlying causes of cell death after cardiac delivery are not completely elucidated. Three general mechanism seem likely to contribute to this cell death: ischemia, anoikis (apoptosis induced by loss of matrix attachments), and host inflammatory reaction.

Cardiomyocytes are among the most ischemia-susceptible cell types in the body. After intracardiac injection, engrafted cardiomyocytes are known to form variously sized clumps within tissue interstices. Because these clumps are avascular, the cells within them must rely on diffusion for nutrient transport and metabolic waste exchange, a problematic situation given that the critical diffusion limit of 100 microns is often exceeded. Indeed, ultrastructural studies have demonstrated signs of irreversible ischemic injury in myocytes within 24 hours of implantation (i.e. severe cytoplasmic and mitochondrial swelling, formation of amorphous mitochondrial matrix densities).

Anoikis is a contributor to cell death as well. Cardiomyocytes are normally surrounded by a basal lamina, to which they bind via integrins and other receptor molecules. The latter transmit pro-survival signals (in part mediated through NF-κB pathway). When cells are enzymatically dispersed for injection, they have typically been suspended in protein-free medium. While so detached, the cells are denied critical survival signals, resulting initiation of pro-death signaling cascades that are directly attributable to loss of matrix attachments. This situation is not restored until after implantation, by when the cells have had time to spread and re-attach within their new environment.

The third major cause of graft cell death is host-mediated inflammation. This inflammatory reaction need not be limited to immune rejection of the graft by the host; indeed, much inflammation-related cell death occurs prior to the mounting of graft immunity. This is because the healing myocardial infarct is an intrinsically inflammatory milieu and thus is hostile even for syngeneic graft cells. For the first few days, the infarct zone contains abundant infiltrating neutrophils, while macrophages predominate at later timepoints. Leukocytes produce oxygen-derived free radicals and inflammatory cytokines that can directly damage the graft cells and/or initiate signaling pathways resulting in caspase activation.

The causes of graft cardiomyocyte death may be complex and multfactorial. Indeed, although hESC-derived cardiomyocytes can reliably form new human myocardium after implantation in uninjured rat hearts, it has been difficult to obtain similar graft survival within infarcted rat hearts. In the latter case, typically it was found that there were few or no persistent graft cells (at timepoints of 1-4 weeks after implantation). Interventions known to enhance graft cardiomyocyte survival, including heat-shock and adenoviral delivery of the anti-apoptotic molecule bcl-2 were insufficient in improving survival of the engrafted hESC-derived cardiomyocytes within the infarct zone.

The methods of the invention involve the grafting of cells in the presence of a cocktail containing multiple pro-survival molecules (hereafter referred to as "KSM"). In addition, the method includes pre-treatment of the cells to be grafted with a subset of these reagents and systemic treatment of the host to maintain therapeutic levels of selected reagents during the window of graft susceptibility. Table 1 (see below) lists the reagents included in KSM as well as their mechanism(s) of action.

24 hours prior to grafting, cells were heat-shocked with a simple 30 minute transition to 43° C., and then returned to 37° C. medium supplemented with IGF-1 and cyclosporine A (at the same concentrations as in KSM injectate).

Cells are harvested as per Xu et al. (2002) Circ Res 91:501-508, except that all media in contact with the cells is supplemented with ZVAD (10 μM), Bcl-$X_L$ BH4 (50 nM), cyclosporine (0.2 μM), IGF-1 (100 ng/ml), and pinacidil (50 μM).

Cells are injected into the myocardium in the presence of 50% (v/v) Matrigel, supplemented with ZVAD (100 μM), Bcl-$X_L$ BH4 (50 nM), cyclosporine (0.2 uM), IGF-1 (100 ng/ml), and pinacidil (50 uM).

To maintain a therapeutic level of cyclosporine in the milieu of the engrafted cells throughout the time period in which necrosis due to ischemic/reperfusion injury is likely, the recipient is dosed with 2.5 mg/kg/day CyA IM, starting 1 day prior to grafting and continuing for 7 days after grafting.

TABLE 1

| Components | |
| --- | --- |
| | Mechanism of Action |
| Matrigel | Solubilized basement membrane preparation (Kleinman and Martin GR (2005): Semin Cancer Biol) opposes anoikis (by providing laminin, collagen, and other attachment factors) |
| ZVAD-FMK | Cell-permeable irreversible pan-caspase inhibitor, (Fearnhead et al. (1995) FEBS Lett 357: 242-246) prevents caspase-mediated cell death of myocytes (Malhotra et al. (1999) J Biol Chem 1274: 12567-12575) |
| Bcl-$X_L$ BH4 (TAT-BH4) | Cell-permeable form of the BH4 peptide domain of Bcl-$X_L$ inhibits apoptotic cell death by blocking the mitochondrial voltage-dependent anion channel (Shimizu et al. (2000) Proc Natl Acad Sci USA 97: 3100-3105) |
| Cyclosporine A | Inhibitor of mitochondrial cyclophilin D suppresses myocyte necrotic cell death due to ischemic injury |
| IGF-1 | Endogenous glycoprotein that promotes myocyte proliferation and opposes hypoxia-induced myocyte apoptosis (Reiss et al. (1997) Exp Cell Res 235: 198-209; Mehrhof et al. (2001) Circulation 104: 2088-2094 |
| Pinacidil | Small-molecule $K_{ATP}$ channel opener promotes myocyte survival during oxidative stress or ischemia-reperfusion injury (Vanden Hoek et al. (2000) Circ Res 86: 541-548) |

Results

The ability of KSM to improve graft outcome following the implantation of hESC-derived cardiomyocytes was tested, using a modification of a previously described nude (athymic) rat model (Laflamme et al. (2005) Am J Pathol). In brief, infarcts were performed by transiently occluding the left anterior descending coronary artery (60 minutes total ischemic time), followed by reperfusion. 4 days later, each rat underwent a second thoracotomy and direct intracardiac injection of 5×10⁶ of the aforementioned cells either in serum-free medium, Matrigel alone, or KSM cocktail. Cells in all three experimental arms were heat-shocked via a 30 minute exposure to 43° C. medium. Hearts were evaluated 1 week after grafting and, as illustrated by FIG. 1, the results were dramatic. While none of the grafts delivered in serum-free medium survived, all hearts receiving cells in either Matrigel or KSM showed surviving grafts. KSM-delivered grafts showed a four-fold larger cardiac graft than Matrigel alone.

We examined the ability of KSM to improve graft survival in infarcted hearts at longer timepoints. In this experiment, 11 of 11 rats receiving cells in KSM showed surviving grafts at 4 weeks, a much better survival rat than the 2 of 12 rats receiving cells in serum-free medium.

The compositions and procedures provided in the description can be effectively modified by those skilled in the art without departing from the spirit of the invention embodied in the claims that follow.

The invention claimed is:

1. A method for the transplantation of mammalian cells, the method comprising:
   administering to an individual a cellular composition comprising mammalian cells selected from stem cells, progenitor cells and cardiomyocytes in a fluid suspension comprising solubilized basement membrane proteins, an immunosuppressive agent, a pan-caspase inhibitor, an anti-apoptotic agent, IGF-1, and a $K_{ATP}$ channel opening agent,
   wherein said mammalian cells are heat-shocked prior to said transplantation.

2. The method according to claim 1, wherein said mammalian cells are cultured in vitro.

3. The method according to claim 1, wherein said mammalian cells are derived from embryonic stem cells in vitro.

4. The method according to claim 3, wherein said mammalian cells are cardiomyocytes.

5. The method according to claim 1, wherein said mammalian stem or progenitor cells are cultured in the presence of an anti-inflammatory agent and an IGF1R ligand prior to said transplantation.

6. The method according to claim 1, wherein the solubilized basement membrane protein is present at a concentration of from 2.5 mg/ml to 8 mg/ml.

7. The method according to claim 1, wherein the immunosuppressive agent is cyclosporine, and is present at a concentration of at least 10 nM and not more than 1 μM.

8. The method according to claim 1, wherein the pan-caspase inhibitor is present at a concentration of at least 2.5 mg/ml and not more than 8 mg/ml.

9. The method according to claim 1, wherein the IGF-1 is present at a concentration of at least 1 μg/ml and not more than 1 μg/ml.

10. The method according to claim 1, wherein the anti-apoptotic agent is the BH4 peptide domain of Bcl-$X_L$ at a concentration of at least 0.1 nM and not more than 10 μM.

11. The method according to claim 1, wherein the $K_{ATP}$ channel opening agent is pinacidil at a concentration of at least 1 μM and not more than 1 mM.

12. A method for the transplantation of mammalian cardiomyocytes, the method comprising:
    administering to an individual a cellular composition comprising cardiomyocytes cultured in vitro in the presence of an anti-inflammatory agent and an IGF1R ligand; in a fluid suspension comprising solubilized basement membrane proteins, an immunosuppressive agent, a pan-caspase inhibitor, an anti-apoptotic agent, IGF-1, and a $K_{ATP}$ channel opening agent,
    wherein said mammalian cells are heat-shocked prior to said transplantation.

13. The method according to claim 12, wherein the solubilized basement membrane protein is present at a concentration of from 2.5 mg/ml to 8 mg/ml.

14. The method according to claim 12, wherein the immunosuppressive agent is cyclosporine, and is present at a concentration of at least 10 nM and not more than 1 μM.

15. The method according to claim 12, wherein the pan-caspase inhibitor is present at a concentration of at least 2.5 mg/ml and not more than 8 mg/ml.

16. The method according to claim 12, wherein the IGF-1 is present at a concentration of at least 1 ng/ml and not more than 1 μg/ml.

17. The method according to claim 12, wherein the anti-apoptotic agent is the BH4 peptide domain of Bcl-$X_L$ at a concentration of at least 0.1 nM and not more than 10 μM.

18. The method according to claim 12, wherein the $K_{ATP}$ channel opening agent is pinacidil at a concentration of at least 1 μM and not more than 1 mM.

* * * * *